United States Patent [19]

Walker

[11] 4,204,424
[45] May 27, 1980

[54] CHROMATOGRAPHIC ANALYZER DETECTOR GAIN ADJUSTMENT

[75] Inventor: Starnes E. Walker, Bartlesville, Okla.

[73] Assignee: Phillips Petroleum Company, Bartlesville, Okla.

[21] Appl. No.: 1,980

[22] Filed: Jan. 8, 1979

[51] Int. Cl.² ............................................. G01N 31/08
[52] U.S. Cl. ...................................... 73/23.1; 250/345
[58] Field of Search ....................... 73/23.1; 23/232 C; 422/89, 91; 250/343, 345, 565; 356/51, 323; 340/632

[56] References Cited

U.S. PATENT DOCUMENTS

| | | | |
|---|---|---|---|
| 3,897,154 | 7/1975 | Hawes | 73/23.1 |
| 4,158,772 | 6/1979 | Reedy | 250/343 |

OTHER PUBLICATIONS

Schweber, B.; "Two-Color LED Pair Is Digital Status Indicator"; Electronic Designers Casebook, *Electronics*, p. 127.
Mazur, T.; "Analog Voltage Sensor Controls LED Threshold," Electronic Designers Casebook, *Electronics*, p. 51.
Franco, S.; "LED Display Shows Beat Frequency," Electronic Designers Casebook, *Electronics*, p. 42.
"Spectra-Physics SP8200 Dual Beam UV/Visible Detector".

*Primary Examiner*—Stephen A. Kreitman

[57] ABSTRACT

A method and apparatus for adjusting the gain of the sample and reference outputs of a chromatographic analyzer detector with respect to a reference voltage is provided. The detector sample output is compared to a voltage reference and this comparison is utilized to drive a dual color light-emitting diode. The light-emitting diode emits a first color when the gain is too high and emits a second color when the gain is too low. When the gain is correctly set so that the sample output is equal to the reference voltage when only carrier fluid is flowing through the sample side of the chromatographic analyzer detector, the light-emitting diode emits no light, thereby indicating that the gain is correctly set. A corresponding procedure is utilized to set the gain of the reference side of the chromatographic analyzer detector. The light-emitting diodes are also particularly useful as a diagnostic aid in optical absorbence chromatographic analyzer detector systems.

10 Claims, 2 Drawing Figures

CHROMATOGRAPHIC ANALYZER DETECTOR GAIN ADJUSTMENT

This invention relates to chromatography. In a particular aspect this invention relates to method and apparatus for balancing the sample and reference outputs of a chromatographic analyzer detector with respect to a reference voltage. In another particular aspect this invention relates to method and apparatus for diagnosing problems associated with an optical absorbence chromatographic analyzer detector.

A chromatographic analyzer is an analytical instrument that is used to separate in time and individually detect the constituents of a sample to be analyzed. The chromatographic analyzer typically includes an analytical column through which a carrier fluid is passed continuously. The sample to be analyzed is injected into the carrier stream and is thus carried through the analytical column. The sample constituents are carried through the analytical column at different velocities and in this manner the sample constituents are separated in time.

A detector is employed to detect the separated constituents and the detector output signal typically is plotted as a function of time to produce what is termed a chromatogram. As each sample component is eluted from the column the component produces a sharp increase in the detector output signal amplitude, which increase appears as a peak or spike in the chromatogram.

There are many different types of chromatographic analyzer detectors. Generally, chromatographic analyzer detectors are made up of a sample side and a reference side. Carrier fluid flows through the reference side. Carrier fluid containing the injected sample flows through the sample side of the detector. Some characteristics such as optical absorbence, thermal conductivity or refractive index of the carrier alone is compared to the same characteristic of the carrier containing the sample. The detector output signal amplitude will vary in response to the differences between the carrier fluid and the carrier fluid containing the sample. In this manner, an analysis of the individual components in the sample may be obtained.

Because the analysis is based on the comparison of the output signal from the reference side of the detector to the output signal from the sample side of the detector, it is necessary that the two output signals be equal when the same material is flowing through both the reference side and the sample side of the detector. It is thus an object of this invention to provide method and apparatus for balancing the sample and reference outputs of a chromatographic analyzer detector with respect to a reference voltage.

An optical absorbence detector is based on the principal that light is absorbed differently by different materials. In an optical absorbence detector system, light at a particular wavelength is passed through the carrier fluid and is also passed through the carrier fluid containing the sample. The difference in the intensity of the light passing out of the carrier fluid and the light passing out of the carrier fluid containing the sample provides an indication of the concentration of a particular component in the sample. However, if the lenses through which the light is passed into the carrier fluid and the carrier fluid containing the sample become fogged or if the intensity of the light source varies, the accuracy of the analysis is affected. It is also possible that an air bubble may pass through either the reference side or the sample side of the detector and this may also affect the analysis. It is thus desirable to have a diagnostic tool which will indicate when a problem has occurred with an optical absorbence detector. It is therefore a particular object of this invention to provide method and apparatus for diagnosing problems associated with an optical absorbence chromatographic analyzer detector.

In accordance with the present invention, method and apparatus is provided whereby the output of the sample side of a detector is compared to a reference voltage when only carrier fluid is flowing through the sample side of the detector. This comparison is utilized to drive a two-color light-emitting diode (LED). If the output of the sample side of the detector is higher than the reference voltage then the LED emits the first color. It the output of the sample side of the detector is lower than the reference voltage then the LED emits a second color. When the output of the sample side of the detector is substantially equal to the reference voltage the LED emits no color.

In the same manner the reference output of the detector is compared to the same reference voltage when only carrier fluid is flowing through the sample side of the detector and this comparison is utilized to drive a second two-color LED. This second two-color LED also emits first and second colors or no color, depending on whether the reference output from the detector is higher than, lower than or substantially equal to the reference voltage. In this manner, the sample output of the detector may be set substantially equal to the reference output of the detector when only carrier fluid is flowing through the sample side and reference side of the detector. Carrier fluid containing sample can then be introduced into the sample side of the detector and the difference between the sample output and the reference output of the detector provides an accurate indication of the concentration of particular components in the sample.

When an optical absorbence detector is being utilized as the chromatographic analyzer detector, the two two-color LEDs provide a valuable diagnostic tool. If the lenses in the optical absorbence detector become fogged or if the intensity of the light source in the optical absorbence detector begins to decrease, the two-color LEDs will indicate this by turning on. The two-color LEDs will also indicate when an air bubble is passing through either the reference side or the sample side of the detector.

Other objects and advantages of the invention will be apparent from the description of the invention and the appended claims as well as from the detailed description of the drawings in which:

The invention is described in terms of a specific chromatographic analyzer system and an optical absorbence detector. The invention is, however, applicable to other chromatographic analyzer systems and configurations and is also applicable to other types of detectors such as thermal conductivity detectors, dielectric constant detectors or refractive index detectors.

The invention is also described in terms of a particular electrical circuit in which a two-color LED is utilized. Two single-color LEDs could be utilized if desired and different colors could be utilized if desired. It is also noted that the invention is described in terms of turning the two-color LED off when either the reference output or the sample output is equal to the reference voltage. However, the LED could be biased to provide a particular color when the outputs are equal to the reference voltage if desired.

Figure 1:
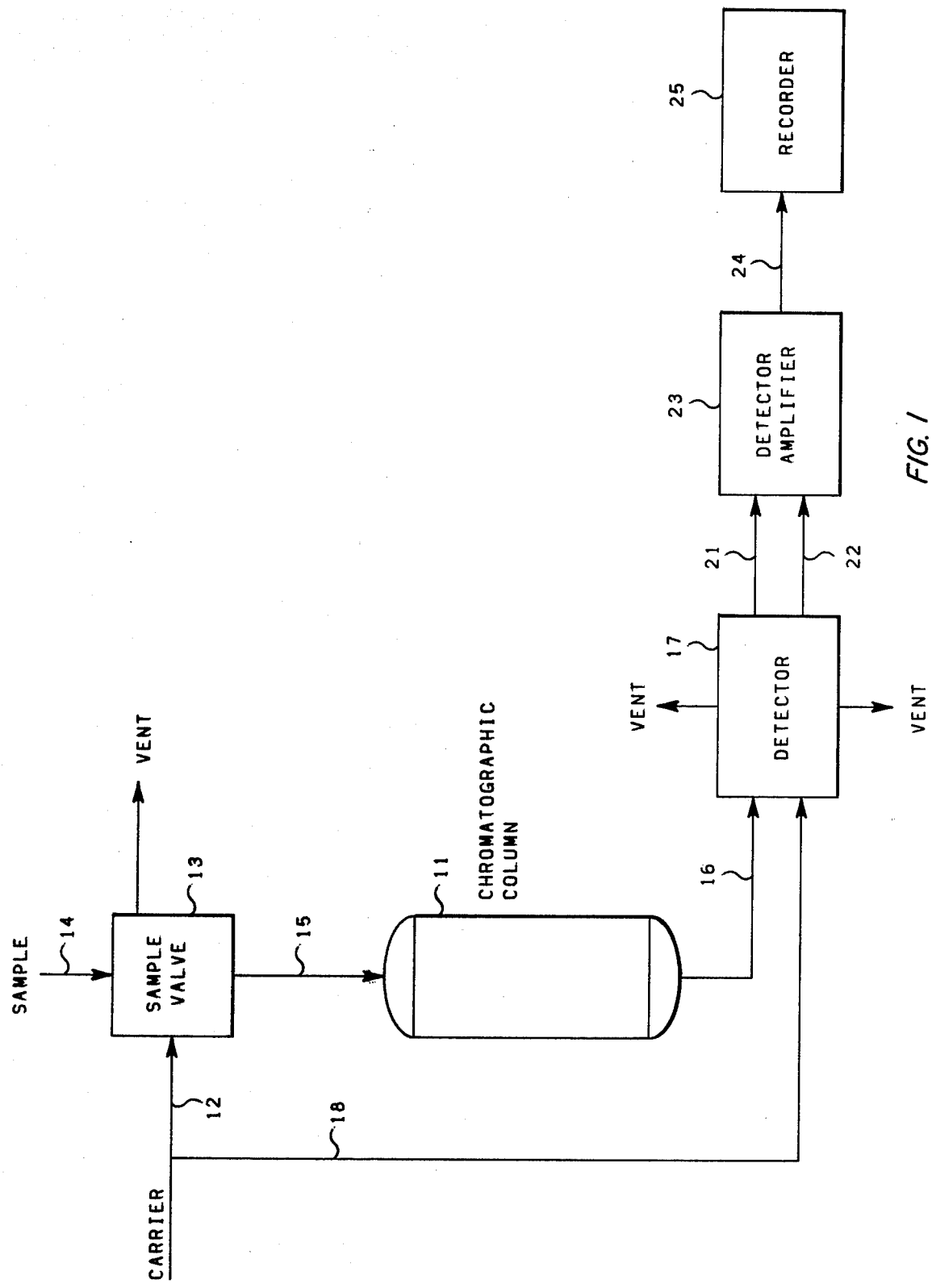
FIG. 1 is a representation of a chromatographic analyzer system.

Referring now to the drawings and in particular to FIG. 1, there is shown a chromatographic column 11. A carrier fluid is introduced through conduit means 12 into sample valve 13. A sample of a fluid to be analyzed is delivered to sample valve 13 through conduit means 14. A conduit means 15 extends between sample valve 13 and the inlet to chromatographic column 11. A conduit means 16 extends between the outlet of chromatographic column 11 and the first inlet of a detector means 17. Carrier fluid is passed through the reference portion of detector means 17 by being introduced into the second inlet of detector means 17 through conduit means 18 which communicates with conduit means 12. Carrier fluid also flows through sample valve 13 and chromatographic column 11 to the first inlet of detector means 17.

At the beginning of an analysis period, sample valve 13 is actuated to introduce a predetermined volume of sample into the carrier fluid flowing through chromatographic column 11. The constituents of the sample are eluted in sequence and flow from the chromatographic column 11 through conduit means 16 to the sample portion of detector means 17.

Detector means 17 establishes a differential output by establishing an electrical signal 21 representative of the composition of the carrier fluid carrying the sample passing through the sample portion of detector means 17 and an electrical signal 22 representative of the composition of the carrier fluid only in the reference portion of detector means 17. Signals 21 and 22 are then compared by detector amplifier 23 to produce signal 24 representative of a chromatographic analyzer output signal. Signal 24 is supplied to recording means 25 where it is stored.

Figure 2:
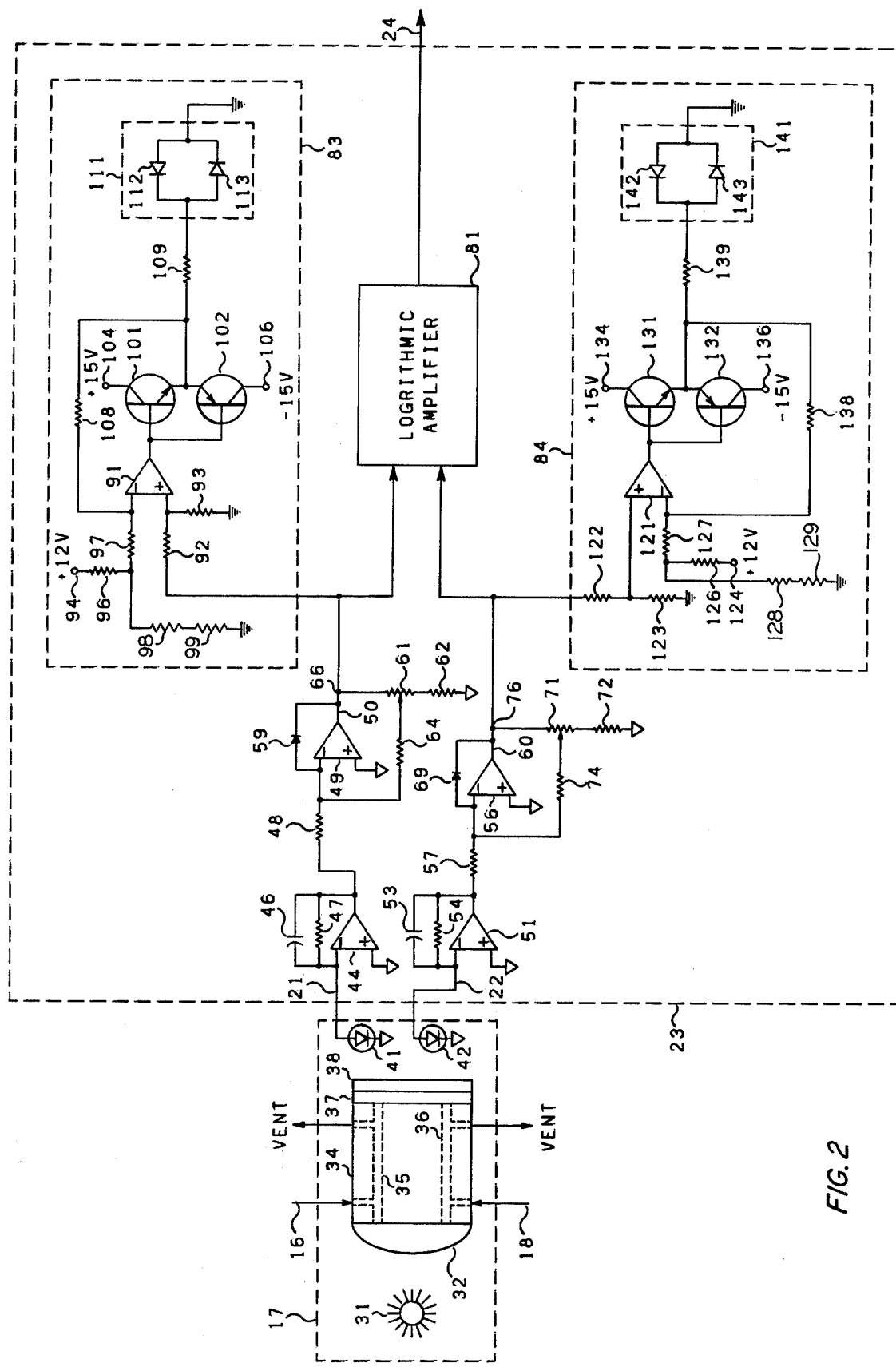
FIG. 2 is a representation of the detector and detector amplifier of the chromatographic analyzer system illustrated in FIG. 1.

The detector 17 and the detector amplifier 23, illustrated in FIG. 1, are more fully illustrated in FIG. 2. Referring now to FIG. 2, detector means 17 is preferably an optical absorbence detector. The light source 31 is preferably a mercury lamp. Light is radiated spherically from the mercury lamp 31 and strikes the collimating quartz lens 32. The light radiating from the light source 31 is refracted by the collimating quartz lens 32 so as to provide light through the sample and reference flow cell 34 substantially parallel to the walls of conduits 35 and 36 which are located inside the sample and reference flow cell 34.

A quartz plate 37 and an interference filter 38 are provided to both seal the sample and reference flow cell 34 and to filter out unwanted wavelengths of light. The interference filter 38 allows the measurement of only the light at a specific wavelength which was absorbed. The collimating quartz lens 32 and the quartz plate 37 may be sealed to the sample and reference flow cell by direct compression of the Tefzel cell body. An O-ring is preferably placed between the interference filter 38 and the quartz plate 37.

The silicon photodiode 41 is located so that the light passing through conduit 35 will impinge on the silicon photodiode 41. The silicon photodiode 42 is located so that the light passing through the conduit 36 will impinge on the silicon photodiode 42. The intensity of the light at a particular wavelength which strikes the silicon photodiodes 41 and 42 will provide an indication of the relative absorption of the carrier fluid flowing through conduit means 36 and the carrier fluid plus sample which flows through conduit means 35. Signal 21 is thus a representation of the light which was absorbed by the carrier fluid plus sample. Signal 22 is a representation of the light which was absorbed by only the carrier fluid.

Signal 21 is provided from the anode side of the silicon photodiode 41 to the inverting input of the operational amplifier 44. The noninverting input of the operational amplifier 44 is tied to ground. The output of the operational amplifier 44 is fed back to the inverting input of the operational amplifier 44 through the parallel combination of capacitor 46 and resistor 47. The output from operational amplifier 44 is also provided through resistor 48 to the inverting input of operational amplifier 49. Operational amplifier 44 provides amplification for signal 21 which will be a very small electrical current typically in the nanoamp range.

In like manner, signal 22 is provided to the inverting input of operational amplifier 51. The noninverting input of operational amplifier 51 is tied to ground. The output from operational amplifier 51 is fed back to the inverting input of operational amplifier 51 through the parallel combination of capacitor 53 and resistor 54. The output from operational amplifier 51 is also provided to the inverting input of operational amplifier 56 through resistor 57. Operational amplifier 51 is utilized to amplify signal 22 which will also be a very small electrical current typically in the nanoamp range.

The noninverting input of operational amplifier 49 is tied to ground. The output of operational amplifier 49 is fed back to the inverting input of operational amplifier 49 through diode 59. The output from the operational amplifier 49 is also tied to one terminal of the potentiometer 61. A second terminal of the potentiometer 61 is tied to ground through resistor 62. The wiper of potentiometer 61 is tied to the inverting input of operational amplifier 49 through resistor 64. Operational amplifier 49 and potentiometer 61 provides a means by which the gain of the sample output 21 from the detector 17 may be varied. The setting of the potentiometer 61 determines the voltage level which will appear at node 66.

The noninverting input of operational amplifier 56 is tied to ground. The output of operational amplifier 56 is fed back to the inverting input of operational amplifier 56 through diode 69. The output from the operational amplifier 56 is also tied to one terminal of the potentiometer 71. A second terminal of the potentiometer 71 is tied to ground through resistor 72. The wiper of potentiometer 71 is tied to the inverting input of operational amplifier 56 through resistor 74. Operational amplifier 56 and potentiometer 71 provides a means by which the gain of the reference output 22 from the detector 17 may be varied. The setting of the potentiometer 71 determines the voltage level which will appear at node 76.

The output signal 50 from the operational amplifier 49, which is representative of the amplified output signal 21 from the optical absorbence detector 17, is provided as a first input to the logarithmic amplifier 81. In like manner, the output signal 60 from operational amplifier 56, which is representative of the amplifier output signal 22 from the optical absorbence detector 17, is provided as a second input to the logarithmic amplifier 81. The logarithmic amplifier 81 is preferably a 4127KG manufactured by Burr-Brown. The logarithmic amplifier 81 provides an output signal 24 which is substantially equal to the log of the voltage level of the output signal 50 from operational amplifier 49 divided by the voltage level of the output signal 60 from operational amplifier 56. Signal 24 is provided to recorder 25 as is illustrated in FIG. 1.

As has been previously stated, the output signal 24 will be meaningless unless signal 50 is substantially equal to signal 60 when only carrier fluid is flowing through both conduit means 36 and conduit means 35. Balancing circuits 83 and 84 are utilized to insure that the voltage level of signal 50 is substantially equal to the voltage level of signal 60 when only carrier fluid is flowing through both conduit means 36 and conduit means 35.

The output signal 50 from operational amplifier 49 is supplied to the noninverting input of operational amplifier 91 through resistor 92 which is in parallel with resistor 93. The inverting input of operational amplifier 91 is tied to the reference voltage 94 through the series/parallel combination of resistors 96, 97, 98 and 99. The output from the operational amplifier 91 is tied to both the base of transistor 101 and the base of transistor 102. The collector of transistor 101 is tied to the +15 volt power supply 104. The emitter of the transistor 101 is tied to the emitter of transistor 102. The collector of transistor 102 is tied to the −15 volt power supply 106. Both the emitter of transistor 101 and the emitter of transistor 102 are tied to the inverting input of operational amplifier 91 through resistor 108. The emitter of transistor 101 and the emitter of transistor 102 are also tied through resistor 109 to the two-color LED 111 which is preferably a Red/Green Tri-State Lamp, MV 5491, Monsanto. The two-color LED 111 is made up of red diode 112 and green diode 113. The cathode of diode 112 and the anode of diode 113 are tied to resistor 109. The anode of diode 112 and the cathode of diode 113 are tied to ground.

The size of resistors 96 and 97 determines the electrical current which will flow from the +12 volt power supply 94 through resistor 97. The electrical current flowing through resistor 92, which is determined by the voltage level of the sample output 50, is balanced with respect to the current flowing through resistor 97. Operational amplifier 91 is a high gain amplifier because a 10 megohm resistor is preferably utilized for resistor 108 with a 100 K ohm resistor being utilized for resistor 97. Thus, if the current being supplied through resistor 92 is slightly greater than the current being supplied through resistor 97, the output from the operational amplifier 91 will turn the NPN transistor 101 on. This will cause the green LED 113 to turn on and a green light will be visible from the two-color LED 111.

If the current supplied through resistor 97 is slightly greater than the current supplied through resistor 92, then the output from the operational amplifier 91 will cause the PNP transistor 102 to turn on. This will in turn cause the red LED 112 to turn on and a red light will be visible from the two-color LED 111.

If the current supplied through resistor 97 is substantially equal to the current supplied through resistor 92 to within approximately ±0.5 percent, then neither transistor 101 nor transistor 102 will be turned on by the output from the operational amplifier 91. In turn, neither diode 112 nor diode 113 will be turned on and no light will be visible from the LED 111. No light from the LED 111 thus provides an indication that the gain has been correctly set. The gain of the sample side of the detector amplifier may be set by varying the setting of potentiometer 61 as has been previously stated.

The output signal 60 from operational amplifier 56 is supplied to the noninverting input of operational amplifier 121 through resistor 122 which is in parallel with resistor 123. The inverting input of operational amplifier 121 is tied to the reference voltage 124 through the series/parallel combination of resistors 126, 127, 128 and 129. The output from the operational amplifier 121 is tied to both the base of transistor 131 and the base of transistor 132. The collector of transistor 131 is tied to the +15 volt power supply 134. The emitter of the transistor 131 is tied to the emitter of transistor 132. The collector of transistor 132 is tied to the −15 volt power supply 136. Both the emitter of transistor 131 and the emitter of transistor 132 are tied to the inverting input of operational amplifier 121 through resistor 138. The emitter of transistor 131 and the emitter of transistor 132 are also tied through resistor 139 to the two-color LED 141 which corresponds to LED 111. The two-color LED 141 is made up of red diode 142 and green diode 143. The cathode of diode 142 and the anode of diode 143 are tied to resistor 139. The anode of diode 142 and the cathode of diode 143 are tied to ground.

The size of resistors 126 and 127 determines the electrical current which will flow from the +12 volt power supply 134 through resistor 127. The electrical current flowing through resistor 122, which is determined by the voltage level of the sample output 60, is balanced with respect to the current flowing through resistor 127. Operational amplifier 121 is a high gain amplifier because a 10 megohm resistor is preferably utilized for resistor 138 with a 100 K ohm resistor being utilized for resistor 127. Thus, if the current being supplied through resistor 122 is slightly greater than the current being supplied through resistor 127 the output from the operational amplifier 121 will turn the NPN transistor 131 on. This will cause the green LED 143 to turn on and a green light will be visible from the two-color LED 141.

If the current supplied through resistor 127 is slightly greater than the current supplied through resistor 122, then the output from the operational amplifier 121 will cause the PNP transistor 132 to turn on. This will in turn cause the red LED 142 to turn on and a red light will be visible from the two-color LED 141.

If the current supplied through resistor 127 is substantially equal to the current supplied through resistor 122 to within approximately ±0.5 percent, then neither transistor 131 nor transistor 132 will be turned on by the output from the operational amplifier 121. In turn, neither diode 142 nor diode 143 will be turned on an no light will be visible from the LED 141. No light from the LED 141 thus provides an indication that the gain has been correctly set. The gain of the reference side of the detector amplifier may be set by varying the setting of potentiometer 71 as has been previously stated.

When it is desired to operate the chromatographic analyzer system illustrated in FIG. 1, carrier fluid is first provided through both the reference side and the sample side of the detector 17. Potentiometer 61 is varied until no light is visible from the LED 111. In like manner, potentiometer 71 is varied until no light is visible from the LED 141. In this manner, the sample output and the reference output are balanced to within approximately ±0.5 percent when only carrier fluid is flowing through the reference side and the sample side of the detector. The detector can then be utilized to analyze a sample and the circuit will remain balanced for a substantial period of time.

As has been previously stated, the LEDs 111 and 141 and their associated circuitry may be utilized as diagnostic tools. If the intensity of the light source 31 begins to decrease, both the LED 111 and the LED 141 will begin to emit a red color. In like manner when deposits build up on the quartz lenses 32 or 37, the LEDs will begin to emit a red color. Since deposits will typically build up only on the sample side of the detector, only the LED 111 will begin to emit a red color and this is an indication that deposits are building up on the quartz lens 32 or the quartz plate 37.

If an air bubble passes through either the reference side or the sample side of the detector, either LED 111 or LED 141 will begin to emit a red color. In like manner when a sample passes through the sample side of the detector, LED 111 will begin to emit a red color. The LEDs 111 and 141 can thus be utilized as a diagnostic tool for the optical absorbence detector 17.

The invention has been described in terms of its presently preferred embodiment as is shown in FIGS. 1 and 2. For the sake of convenience, signals which supply power to the various chips shown in the schematic of FIG. 2 have been omitted. Voltage levels required by the various chips are specified by the manufacturer and are well known to those familiar with the art.

Many different circuit configurations are possible which would perform the functions required of the circuit shown in FIG. 2. FIG. 2 is illustrative of a particular circuit configuration which will perform the required function.

Specific components which are available commercially and which can be used in the practice of the invention as shown in FIG. 2 follow. Values of resistors and capacitors used in these particular circuits are also given. Again, many different combinations of circuit values, particularly in the areas of resistance and capacitance values, are possible.

| Optical absorbence detector 17 | Applied Automation, Inc. Bartlesville, OK 74004 |
|---|---|
| Operational amplifiers 44 and 51 | 3528BM Burr Brown |
| Operational amplifiers 49 and 56 | OP-10EY Precision Monolithics |
| Operational amplifiers 91 and 121 | MC1458 Motorola |
| Logarithmic amplifier 81 | 4127KG, Burr-Brown |
| Transistors 101 and 131 | 2N3904, National Semiconductor |
| Transistors 102 and 132 | 2N3906 National Semiconductor |
| LEDs 111 and 141 | 5491, Monsanto |
| Resistors 47 and 54 | 200 M MOX1125A, Victoreen |
| Resistors 48,57,97,122,127,99 and 129 | 100 K ohms, RN 60 D, Dale |
| Resistors 64 and 74 | 25.5 K ohms, RN 60 D, Dale |
| Resistors 62 and 72 | 1 K ohm, RN 60 D, Dale |
| Resistors 93, 108, 123 and 138 | 10 megohms, RN 60 D, Dale |
| Resistors 96 and 126 | 1.37 K ohms, RN 60 D, Dale |
| Resistors 98 and 128 | 909 ohms, RN 60 D, Dale |
| Potentiometers 61 and 71 | 10 K ohms, Series 721, Dale |
| Capacitors 46 and 53 | 500 pf, GP 350, Mallory |
| Diodes 59 and 69 | IN 914 National Semiconductor |

While the invention has been described in terms of the presently preferred embodiment, reasonable variations and modifications are possible by those skilled in the art, within the scope of the described invention and the appended claims. For instance, many different types of detectors could be utilized as the chromatographic analyzer detector. Also different colors of LEDs could be utilized and different LED configurations could be utilized to accomplish the purpose of the present invention. Different chromatographic analyzer systems could be utilized if desired.

That which is claimed is:

1. Apparatus comprising:

a chromatographic analyzer detector means capable of measuring a property of a fluid which is characteristic of the fluid, said chromatographic analyzer detector means having a reference side and a sample side;

means for passing a stream of fluid through the reference side of said chromatographic analyzer detector means, said reference side of said chromatographic analyzer detector means providing a first output signal representative of said property of the stream of fluid flowing through the reference side of said chromatographic analyzer detector means;

first amplifier means;

means for providing said first output signal as an input to said first amplifier means, said first amplifier means providing an amplified first output signal as an output;

means for passing a stream of fluid through the sample side of said chromatographic analyzer detector means, said sample side of said chromatographic analyzer detector means providing a second output signal representative of said property of the stream of fluid flowing through the sample side of said chromatographic analyzer detector means;

second amplifier means;

means for providing said second output signal as an input to said second amplifier means, said second amplifier means providing an amplified second output signal as an output;

means for establishing a reference signal;

means for comparing said amplified first output signal and said reference signal when a first stream of fluid is flowing through said reference side of said chromatographic analyzer detector means and for establishing a third signal responsive to the difference between said amplified first output signal and said reference signal;

a first light-emitting diode means;

means for supplying said third signal to said first light-emitting diode means, said first light-emitting diode means emitting a first color when said amplified first output signal is greater than said reference signal, said first light-emitting diode means emitting a second color when said amplified first output signal is less than said reference signal, said first light-emitting diode means emitting substantially no light when said amplified first output signal is substantially equal to said reference signal;

means for adjusting the gain of said first amplifying means until substantially no light is emitted from said first light-emitting diode means;

means for comparing said amplified second output signal and said reference signal when said first stream of fluid is flowing through said sample side of said chromatographic analyzer detector means and for establishing a fourth signal responsive to the difference between said amplified second output signal and said reference signal;

a second light-emitting diode means;

means for supplying said fourth signal to said second light-emitting diode means, said second light-emitting diode means emitting a first color when said amplified second output signal is greater than said reference signal, said second light-emitting diode means emitting a second color when said amplified second output signal is less than said reference signal, said second light-emitting diode means emitting substantially no light when said amplified second output signal is substantially equal to said reference signal; and means for adjusting the gain of said second amplifying means until substantially no light is emitted from said second light-emitting diode means.

2. Apparatus in accordance with claim 1 wherein said chromatographic analyzer detector means comprises an optical absorbence detector.

3. Apparatus in accordance with claim 2 wherein said first light-emitting diode means and said second light emitting diode means comprise two-color light-emitting diode means.

4. Apparatus in accordance with claim 3 wherein said first color is green and said second color is red.

5. Apparatus comprising:

a chromatographic analyzer detector means capable of measuring a property of a fluid which is characteristic of the fluid, said chromatographic analyzer detector means having a reference side and a sample side;

means for passing a stream of fluid through the reference side of said chromatographic analyzer detector means, said reference side of said chromatographic analyzer detector means providing a first output signal representative of said property of the stream of fluid flowing through the reference side of said chromatographic analyzer detector means;

first amplifier means;

means for providing said first output signal as an input to said first amplifier means, said first amplifier means providing an amplified first output signal as an output;

means for passing said stream of fluid through the sample side of said chromatographic analyzer detector means, said sample side of said chromatographic analyzer detector means providing a second output signal representative of said property of the stream of fluid flowing through the sample side of said chromatographic analyzer detector means;

second amplifier means;

means for providing said second output signal as an input to said second amplifier means, said second amplifier means providing an amplified second output signal as an output;

a first operational amplifier means having an inverting input, a noninverting input and an output;

a first resistive element;

means for electrically connecting said amplified first output signal through said first resistive element to said noninverting input of said first operational amplifier means;

a second resistive element;

means for establishing a reference voltage;

means for electrically connecting said means for establishing a reference voltage through said second resistive element to said inverting input of said first operational amplifier means;

a first NPN transistor;

a first PNP transistor;

means for electrically connecting the output of said first operational amplifier means to the base of said first NPN transistor and to the base of said first PNP transistor;

means for generating a first positive voltage;

means for electrically connecting the collector of said first NPN transistor to said means for generating a first positive voltage;

means for generating a first negative voltage;

means for electrically connecting the collector of said first PNP transistor to said means for generating said first negative voltage;

a third resistive element;

a first two-color light-emitting diode means having a first light-emitting diode with the anode thereof electrically connected to ground and having a second light-emitting diode with the cathode thereof electrically connected to ground;

means for electrically connecting the emitter of said first NPN transistor and the emitter of said first PNP transistor through said third resistive element to the cathode of said first light-emitting diode and to the anode of said second light-emitting diode, said first light-emitting diode emitting a green color when the electrical current supplied through said first resistive element is greater than the electrical current supplied through said second resistive element, said second light emitting diode emitting a red color when the current supplied through said first resistive element is less than the current supplied through said second resistive element, said first dual color light-emitting diode means emitting substantially no color when the current supplied through said first resistive element is substantially equal to the current supplied through said second resistive element;

means for adjusting the gain of said first amplifier means until substantially no light is emitted from said first dual color light-emitting diode means;

a second operational amplifier means having an inverting input, a noninverting input and an output;

a fourth resistive element;

means for electrically connecting said amplified second signal through said fourth resistive element to said noninverting input of said second operational amplifier means;

a fifth resistive element;

means for electrically connecting said means for establishing a reference voltage through said fifth resistive element to said inverting input of said second operational amplifier means;

a second NPN transistor;

a second PNP transistor;

means for electrically connecting the output of said second operational amplifier means to the base of said second NPN transistor and to the base of said second PNP transistor;

means for electrically connecting the collector of said second NPN transistor to said means for generating a first positive voltage;

means for electrically connecting the collector of said second PNP transistor to said means for generating said first negative voltage;

a sixth resistive element;

a second two-color light-emitting diode means having a third light emitting diode with the anode thereof electrically connected to ground and having a fourth light emitting diode with the cathode thereof electrically connected to ground;

means for electrically connecting the emitter of said second NPN transistor and the emitter of said second PNP transistor through said sixth resistive element to the cathode of said third light-emitting diode and to the anode of said fourth light-emitting diode, said second light-emitting diode emitting a green color when the electrical current supplied through said first resistive element is greater than the electrical current supplied through said second resistive element, said fourth light emitting diode emitting a red color when the current supplied through said first resistive element is less than the current supplied through said second resistive element, said second dual color light-emitting diode emitting substantially no color when the current supplied through said first resistive element is substantially equal to the current supplied through said second resistive element; and means for adjusting the gain of said second amplifier means until substantially no light is emitted from said second dual color light-emitting diode means.

6. Apparatus in accordance with claim 5 wherein said chromatographic analyzer detector means comprises an optical absorbence detector.

7. A method for balancing the sample output signal of a chromatographic analyzer detector means with respect to a reference signal and for balancing the reference output signal of a chromatographic analyzer detector means with respect to said reference signal comprising:

passing a first stream of fluid through the reference side of said chromatographic analyzer detector means, said reference side of said chromatographic analyzer detector means providing said reference output signal representative of a property of said first stream of fluid;

passing said first stream of fluid through the sample side of said chromatographic analyzer detector means, said sample side of said chromatographic analyzer detector means providing said sample output signal representative of said property of said first stream of fluid;

amplifying said reference output signal;

amplifying said sample output signal;

comparing the amplified reference output signal to said reference signal and establishing a first signal responsive to the difference between said amplified reference output signal and said reference signal;

driving a first light-emitting diode means in response to said first signal, said first light-emitting diode means emitting a first color when said amplified reference output signal is greater than said reference signal, said first light-emitting diode means emitting a second color when said amplified reference output signal is less than said reference signal, said first light-emitting diode means emitting substantially no light when said amplified reference output signal is substantially equal to said reference signal;

adjusting the gain factor by which said reference output signal is amplified until substantially no light is emitted from said first light-emitting diode means;

comparing the amplified sample output signal to said reference signal and establishing a second signal responsive to the difference between said amplified sample output signal and said reference signal;

driving a second light-emitting diode means in response to said second signal, said second light-emitting diode means emitting a first color when said amplified sample output signal is greater than said reference signal, said second light-emitting diode means emitting a second color when said amplified sample output signal is less than said reference signal, said second light-emitting diode means emitting substantially no light when the voltage level of said amplified sample output signal is substantially equal to the voltage level of said reference signal; and adjusting the gain factor by which said sample output signal is amplified until substantially no light is emitted from said second light-emitting diode means.

8. A method in accordance with claim 7 wherein said chromatographic analyzer detector means comprises an optical absorbence detector.

9. A method in accordance with claim 8 wherein said first light-emitting diode means and said second light emitting diode means comprise two-color light-emitting diode means.

10. A method in accordance with claim 9 wherein said first color is green and said second color is red.

* * * * *